United States Patent
Ray et al.

(10) Patent No.: US 10,966,670 B2
(45) Date of Patent: Apr. 6, 2021

(54) IMAGING SYSTEM AND METHOD FOR DUAL-ENERGY AND COMPUTED TOMOGRAPHY

(71) Applicant: Carestream Health, Inc., Rochester, NY (US)

(72) Inventors: Lawrence A. Ray, Rochester, NY (US); Richard A. Simon, Rochester, NY (US); Levon O. Vogelsang, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 670 days.

(21) Appl. No.: 15/670,292

(22) Filed: Aug. 7, 2017

(65) Prior Publication Data

US 2019/0038238 A1 Feb. 7, 2019

(51) Int. Cl.
*A61B 6/03* (2006.01)
*A61B 6/00* (2006.01)
*A61B 6/10* (2006.01)

(52) U.S. Cl.
CPC ............ *A61B 6/032* (2013.01); *A61B 6/4007* (2013.01); *A61B 6/482* (2013.01); *A61B 6/488* (2013.01); *A61B 6/5205* (2013.01); *A61B 6/105* (2013.01); *A61B 6/545* (2013.01)

(58) Field of Classification Search
CPC .................................................... A61B 6/482
USPC ............................................................ 378/4
See application file for complete search history.

(56) References Cited

U.S. PATENT DOCUMENTS

| | | |
|---|---|---|
| 5,270,926 A | 12/1993 | Tam |
| 5,999,587 A | 12/1999 | Ning et al. |
| 7,602,879 B2 | 10/2009 | Chen et al. |
| 9,224,216 B2 | 12/2015 | Zamyatin et al. |
| 2014/0270450 A1* | 9/2014 | Grass ............... A61B 6/032 382/131 |
| 2015/0036902 A1* | 2/2015 | Zamyatin ........ G06T 7/0012 382/131 |
| 2017/0150936 A1* | 6/2017 | Yoda ................ A61B 6/4233 |
| 2017/0270694 A1* | 9/2017 | Vogelsang ....... G06T 11/008 |

OTHER PUBLICATIONS

Matthias Bertram et al., Directional View Interpolation for Compensation of Sparse Angular Sampling in Cone-Beam CT, IEEE Transactions on Medical Imaging, vol. 28, No. 7, Jul. 2009, pp. 1011-1022.

* cited by examiner

*Primary Examiner* — David P Porta
*Assistant Examiner* — Abra S Fein

(57) ABSTRACT

An imaging method, accesses a set of low-energy projection images and performs a low-energy reconstruction using the low-energy projection images. A synthesized intermediate low-energy projection image is generated. A high-energy reconstruction is performed using a set of high-energy projection images. A synthesized intermediate high-energy projection image is generated. A dual-energy reconstruction is performed using at least one low-energy projection image, the synthesized intermediate low-energy projection image, at least one high-energy projection image, and the synthesized intermediate high-energy projection image.

17 Claims, 9 Drawing Sheets

IMAGING SYSTEM AND METHOD FOR DUAL-ENERGY AND COMPUTED TOMOGRAPHY

FIELD OF THE INVENTION

The invention relates generally to the field of diagnostic imaging and in particular to radiographic volume imaging and image reconstruction techniques using computed tomography (CT) and/or cone-beam computed tomography (CBCT).

BACKGROUND OF THE INVENTION

Digital radiographic volume imaging provides three-dimensional (3D) images that have been reconstructed from a series of 2D images taken over a succession of angles of the X-ray source relative to the detector. Acquisition of the 2D projection images used for cone beam CT can employ a large-area digital detector, such as a digital radiography (DR) detector that is typically used for conventional single projection radiography.

Computed tomography (CT) systems, such as cone beam computed tomography (CBCT) or cone beam CT systems offer considerable promise as one type of diagnostic tool for providing 3D volume images. Cone beam CT systems capture volume data sets using a high frame rate flat panel digital radiography (DR) detector and an X-ray source. The X-ray source and detector are typically affixed to a gantry that revolves about the object to be imaged, with the X-ray source directing, from various points along its orbit around the subject, a divergent cone beam of X-rays toward the subject. The CBCT system captures projection images throughout the source-detector orbit, for example, with one 2D projection image at every angular increment of rotation. The projections are then reconstructed into a 3D volume image using various techniques. Among the most common methods for reconstructing the 3D volume image are filtered back projection (FBP) approaches.

One factor that affects the quality of volume reconstruction relates to the number of 2D projection images acquired. Projection images are generally obtained at evenly spaced angular increments; having images at a sufficient number of angles helps to provide enough data to minimize or eliminate aliasing effects such as view aliasing artifacts, typically appearing in the form of regularly spaced streaks, and other image processing problems.

Each projection image, however, requires exposure of the patient. Thus, although having more 2D projection image data is advantageous for 3D image reconstruction, it would be preferable to reduce the number of 2D projection images that are obtained, thereby reducing exposure risks to the patient. In addition, it would be beneficial to reduce the required scan time in order to help reduce image reconstruction problems due to patient motion.

Dual-energy (DE) imaging has been used as an alternative method for reducing noise content and differentiating various types of imaged anatomy. In conventional DE imaging, sets of low and high kVp exposures of the same anatomy are acquired in close succession, so that their results can readily be combined without requiring extensive registration techniques. This can help with subsequent segmentation of bone features, for example, allowing more accurate interpretation of the x-ray image content. For 3D volume imaging, as provided by CBCT and CT apparatus, there can be significant advantages in providing dual-energy image content for reconstruction and subsequent analysis.

Standard methods of detector acquisition for dual-energy images involve initiating a first image acquisition at a first energy level, reading out the first image information stored in the detector, and then initiating a second image acquisition at a second energy level. The delay between the acquisition of the first and second images due to the time necessary to read out the first image information prior to initiating the second image acquisition may result in artifacts due to patient motion. This problem can be particularly pronounced in CBCT and CT image acquisition where multiple projection images are acquired in a rapid sequence. Motion artifacts, including those related to involuntary action such as breathing, heartbeat, and other movement, can confound the difficulty of subsequent image reconstruction and analysis. It can be difficult to compensate for patient motion, even using techniques such as double-shot acquisition.

Another drawback of conventional DE imaging relates to high dose levels, often as much as 1.5 to 2.5 times higher than standard exposures, depending on the anatomy type.

Thus, there would be advantages to volume imaging methods that can obtain sufficient projection image content for accurate dual-energy 3D volume reconstruction while reducing dosage requirements.

SUMMARY OF THE INVENTION

It is an object of the present disclosure to advance the art of diagnostic 3D volume imaging, with particular emphasis on acquisition and reconstruction of images obtained using dual-energy techniques. Embodiments disclosed herein offer methods that can help to reduce patient exposure levels for 2D projection image acquisition without compromising 3D volume reconstruction results.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to an embodiment of the present disclosure, there is provided an imaging method, comprising: accessing a set of low-energy projection images; performing a low-energy reconstruction using the low-energy projection images; generating a synthesized intermediate low-energy projection image; accessing a set of high-energy projection images; performing a high-energy reconstruction using the high-energy projection images; generating a synthesized intermediate high-energy projection image; and performing a dual-energy reconstruction using at least one low-energy projection image, the synthesized intermediate low-energy projection image, at least one high-energy projection image, and the synthesized intermediate high-energy projection image.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
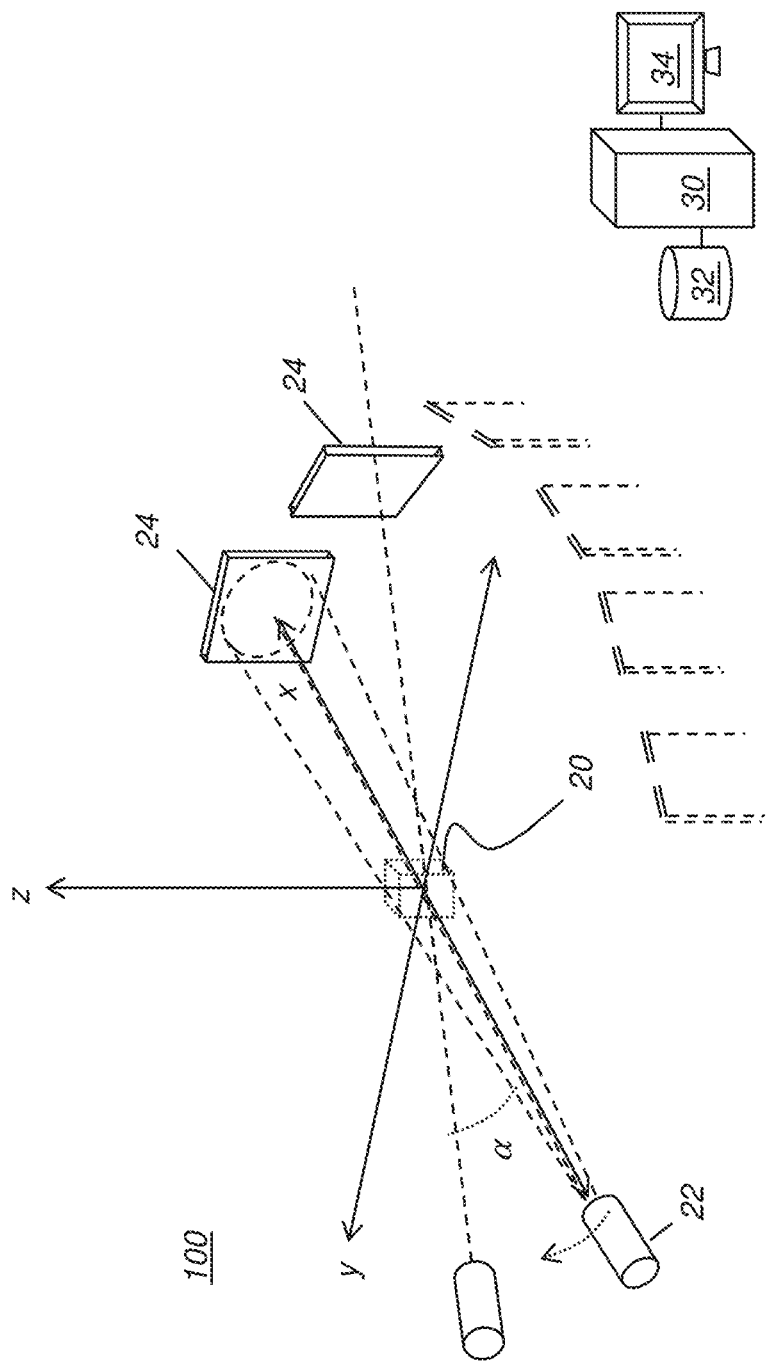
FIG. 1 is a diagram that shows, in schematic form, the scanning activity of a conventional CBCT imaging apparatus.

The following is a detailed description of preferred embodiments of the invention, reference being made to the drawings in which the same reference numerals identify the same elements of structure in each of the several figures.

In the drawings and text that follow, like components are designated with like reference numerals, and similar descriptions concerning components and arrangement or interaction of components already described are omitted. Where they are used, the terms "first", "second", and so on, do not necessarily denote any ordinal or priority relation, but are simply used to more clearly distinguish one element from another.

In the context of the present disclosure, the term "volume image" is synonymous with the terms "3-Dimensional image" or "3D image". Embodiments of the present disclosure are particularly well suited for acquisition of 2D projection images in dual-energy format that can be used for subsequent reconstruction of 3D image content for the subject anatomy.

In the image processing context of the present disclosure, "rendering" is the active process of generating and forming an image for display and generating the pattern of signals needed for displaying it to a user. Image data content that is used for rendering can be transformed from a 2D or 3D model (or models), typically stored as scene content in some type of scene file, into suitable patterns of light energy that are emitted from a display screen. A scene file contains objects in a strictly defined language or data structure, describing aspects of the image content such as geometry, viewpoint, texture, lighting, and shading information as a description of a scene. The data contained in the scene content or scene file is passed to a rendering program to be processed and output or streamed to a display driver or graphics processing unit (GPU) for direct presentation on a display or to a digital image or raster graphics image file. The digital image data file can alternately be available for presentation on a display. In general, the term "rendering" provides a transformation that can be considered as analogous to an "artist's rendering" of a scene; different artists working in different media can generate different renderings of the same scene content. The same image content can be rendered, for example, on a monochrome display or in color on a full color display.

The term "modality" is a term of art that refers to types of imaging. Modalities for an imaging system may be conventional X-ray radiography, fluoroscopy or pulsed radiography, tomosynthesis, tomography, ultrasound, MRI, or other types of imaging. The term "subject" refers to the patient who is being imaged and, in optical terms, can be considered equivalent to the "object" of the corresponding imaging system.

The term "set", as used herein, refers to a non-empty set, as the concept of a collection of elements or members of a set is widely understood in elementary mathematics. The terms "subset" or "partial subset", unless otherwise explicitly stated, are used herein to refer to a non-empty proper subset, that is, to a subset of the larger set, having one or more members. For a set S, a subset may comprise the complete set S. A "proper subset" of set S, however, is strictly contained in set S and excludes at least one member of set S. A "partition of a set" is a grouping of the set's elements into non-empty subsets so that every element is included in one and only one of the subsets. Two sets are "disjoint" when they have no element in common.

With respect to an image detector, the term "pixel" refers to a picture element unit cell containing a photo-conversion circuit and related circuitry for converting incident electromagnetic radiation to an electrical signal. For the image processing steps described herein, the terms "pixels" for picture image data elements, conventionally used with respect 2D imaging and image display, and "voxels" for volume image data elements, often used with respect to 3D imaging, can be used interchangeably.

It should be noted that the 3D volume image is itself generated from image data obtained as pixels on a 2D sensor array and displays as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels.

In the context of the present disclosure, "volume imaging" refers to volume radiographic imaging modalities such as computed tomography (CT) or cone-beam computed tomography (CBCT) imaging. Volume imaging methods form a volume 3D image of a subject that can be viewed as a planar slice or plane section taken at a specified depth and angle. As noted previously, volume imaging obtains 3D depth information by changing the relative angle between the X-ray source and the subject for each 2D projection image that is acquired during scanning.

In the context of the present disclosure, the phrase "in signal communication" indicates that two or more devices and/or components are capable of communicating with each other via signals that travel over some type of signal path. Signal communication may be wired or wireless. The signals may be communication, power, data such as image data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, "acquired" projection images are captured or obtained from scanning the subject with radiation energy. "Synthetic" images are calculated or generated by the system, using data obtained from the acquired images, using procedures described herein.

CBCT imaging apparatus and the imaging algorithms used to obtain 3D volume images using such systems are well known in the diagnostic imaging art and are, therefore, not described in detail in the present application. Some exemplary algorithms and approaches for forming 3D volume images from the source 2D images, projection images that are obtained in operation of the CBCT imaging apparatus can be found, for example, in the teachings of U.S. Pat. No. 5,999,587 entitled "Method of and System for Cone-Beam Tomography Reconstruction" to Ning et al. and of U.S. Pat. No. 5,270,926 entitled "Method and Apparatus for Reconstructing a Three-Dimensional Computerized Tomography (CT) Image of an Object from Incomplete Cone Beam Data" to Tam.

Embodiments of the present invention can be readily adapted to the particular geometry of the CBCT or other volume imaging apparatus. For example, an extremity imaging apparatus that is designed to image anatomy such as feet, ankles, knees, and other extremities can generate volume images suitable for application of methods described herein.

Embodiments of the present disclosure provide approaches for reducing patient exposure and reducing artifacts by acquiring only a partial percentage of the N+M X-ray 2D projection images that would otherwise be needed to for artifact-free reconstruction of an accurate 3D volume image. A number N of projection images are acquired. Then, in order to obtain an ordered set of projection images that is sufficient to be used for tomographic reconstruction, a number of synthesized intermediate projection images M is generated and added to the acquired set of N projection images. This forms a larger set of N+M projection images, effectively providing a reduced angular spacing $\Delta\alpha'$ between adjacent projection images in the sequence used for reconstruction. The result is an enhanced 3D reconstruction that can be substantially artifact-free. This processing can be repeated for reconstructing separate 3D volume images, one from a lower-energy exposure and the other from a higher-energy exposure. Alternately, processing can be used to combine lower- and higher-energy image content for forming a single dual-energy 3D volume image.

Reference is made to an article by Bertram, Wiegert, Schafer, Rose, and Aach entitled "Directional View Interpolation for Compensation of Sparse Angular Sampling in Cone Beam CT" in *IEEE Transactions on Medical Imaging* Vol. 28, No. 7, July 2009, pp. 1011-1022, incorporated herein in its entirety.

Reference is made to U.S. Pat. No. 7,602,879 (Chen et al.) and U.S. Pat. No. 9,224,216 (Zamyatin et al), incorporated herein in their entirety.

In typical applications, a computer or other type of dedicated logic processor for obtaining, processing, and storing image data is part of the CT or CBCT system, along with one or more displays for viewing image results. A computer-accessible memory is also provided, which may be a memory storage device used for longer term storage, such as a device using magnetic, optical, or other data storage media. In addition, the computer-accessible memory can comprise an electronic memory such as a random access memory (RAM) that is used for shorter term storage, such as employed to store a computer program having instructions for controlling one or more computers to practice the method according to the present invention.

In order to more fully understand the methods of the present disclosure and the problems addressed, it is instructive to describe principles and terminology used for CBCT image capture and reconstruction. Referring to the perspective view of FIG. 1, there is shown, in schematic form and using enlarged distances for clarity of description, the activity of a conventional CBCT imaging apparatus 100 for acquiring the individual 2D images that are used to form a 3D volume image. A cone-beam radiation source 22 directs a cone of radiation toward a subject 20, such as a patient or other subject. A sequence of acquired 2D projection images is obtained in rapid succession at varying angles about the subject, such as one image at each 1-degree angle increment in a 200-degree orbit. A digital radiography (DR) detector 24 is moved to different imaging positions about subject 20 in concert with corresponding orbital movement of radiation source 22. FIG. 1 shows a representative sampling of DR detector 24 positions to illustrate how these acquired projection images are obtained relative to the position of subject 20. Once the needed 2D projection images are captured in this sequence, a suitable imaging algorithm, such as filtered back projection (FBP) or other conventional technique, is used for generating the 3D volume image. Image acquisition and program execution are performed by a computer 30 or by a networked group of computers 30 that are in image data signal communication with DR detectors 24. Image processing and storage is performed using a computer-accessible memory 32. The 3D volume image can be rendered for presentation on a display 34.

FBP (filtered back projection) is a discrete implementation of an analytic model that assumes that CT transmission measurements are linear functions of the attenuation line integrals along the corresponding primary photon trajectories through the subject, and assumes that these measurements are noiseless. When scanning subjects comprised of anatomically native materials under normal conditions, relatively simple corrections to the raw projection data are sufficient to assure that these assumptions (i.e. linear relationship) are at least approximately true. This treatment allows acquisition and accurate volume reconstruction without visually observable artifacts.

Embodiments of the present disclosure provide approaches for reducing patient exposure and reducing artifacts with dual-energy imaging by acquiring, for each series of lower-energy images and each series of higher-energy images, a set having a number N of actual, acquired projection images that represents only a partial percentage of the full number (N+M) of X-ray projection images that would otherwise be needed to for artifact-free reconstruction. Then, to obtain a more complete ordered set of projection images that is sufficiently populated for use in tomographic reconstruction, a set having a number of synthesized intermediate projection images M is generated and added to each acquired set of N projection images. For each cycle of lower- and higher-energy acquisitions, this forms a larger set N+M of projection images, effectively providing a reduced angular spacing $\Delta\alpha'$ between adjacent projection images in the sequence used for reconstruction. The result is an enhanced 3D reconstruction for each energy level that can be substantially artifact-free.

As noted previously, dual-energy imaging has emerged as a useful diagnostic tool, with particular value in conjunction with conventional CT. The acquisition process requires the exposure of the patient with two x-ray emissions with different spectral properties, typically from low- and high-energy sources, separately activated. Ideally, the images captured with the two sources can be registered to each other in order to enhance the ability to separate tissue types based upon the images acquired at different energy levels. This capability requires that the patient has been still during the image acquisition phase. In the case of CBCT, the scan time for a single pass is usually between 10-30 seconds, and to make a second pass at a second energy level requires an additional scan, suggesting that the patient remain still for nearly one full minute. This also implies that the patient is subjected to twice the dose of radiation.

An embodiment of the present disclosure addresses difficulties with dual-energy volume imaging by scanning the patient anatomy in a single scan sequence, as described with reference to FIG. 1, but with the radiation energy source or sources toggled in such a way that the low-energy and high-energy radiation is emitted, and corresponding low- and high-energy images acquired, in an alternating cyclical sequence. Thus, to obtain a subset of $N_{low}$ projections for example, low-energy emission would be used, and corresponding projection images acquired. The subset of $N_{low}$ projections can be the even-numbered projections of a larger set, for example. The high-energy emission is then used for the other subset of $N_{high}$ odd-numbered projection images. With this arrangement, overall scan time for full DE volume image acquisition is cut in half, with reduced dose to the patient. In addition, this approach reduces the impact of patient motion on the acquired image content as well as allowing DE imaging at reduce dose levels.

Energy source switching can be accomplished using a number of alternative approaches. The first is to switch an individual x-ray source from low- to high-energy or from high- to low-energy between successive projection captures. This first approach has advantages for simplifying the overall geometry of the scan operation, but requires a source capable of rapidly switching between energy levels. Another approach is to utilize two independent sources, synchronized to be alternately energized for high- and low-energy, respectively as the scan proceeds. This can simplify the problem of source design, but requires providing two separate sources sharing the same imaging path.

Figure 2A:
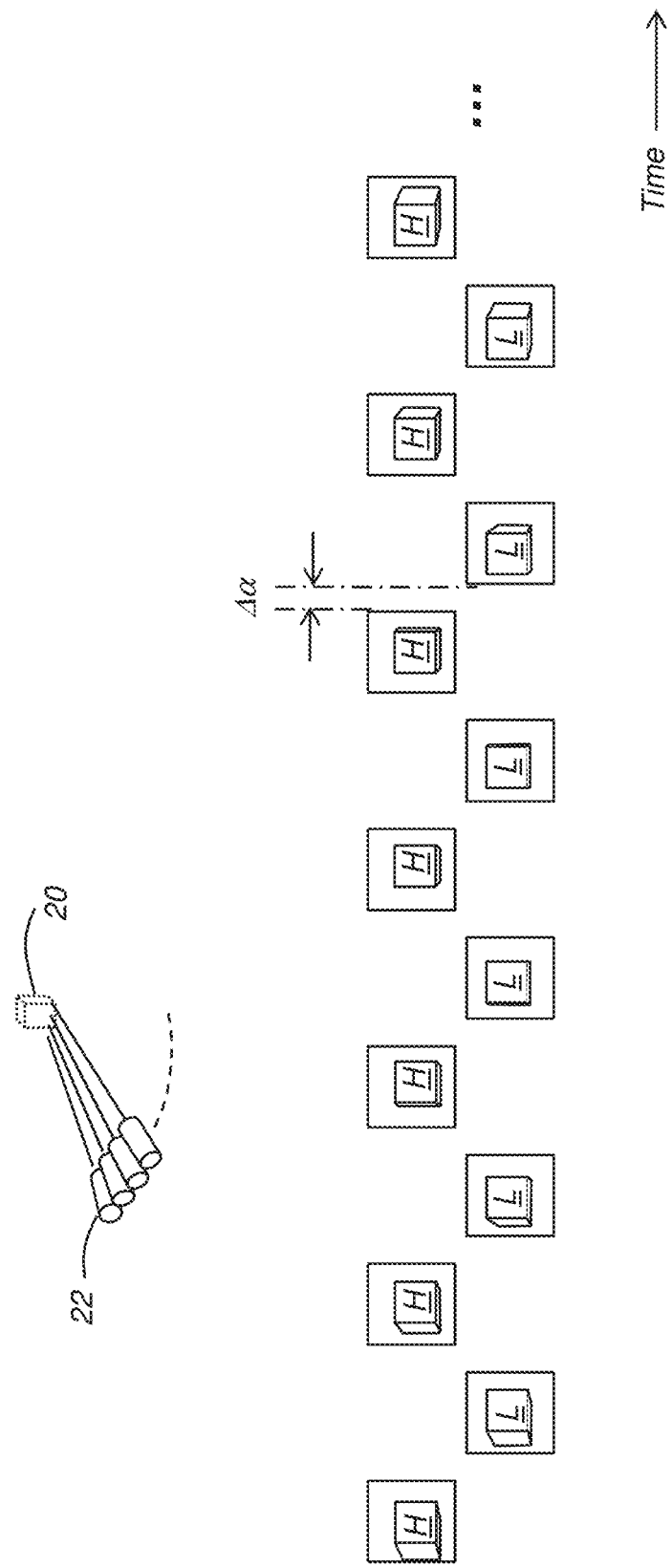
FIG. 2A is a schematic diagram that shows acquisition of a sequence of 2D projection images, with the radiation source alternating between low- and high-energy emission.

The schematic diagram of FIG. 2A shows acquisition of a sequence of 2D projection images, with the radiation source alternating between low- and high-energy emission. Time advances from left to right. High-energy projection images H are interspersed with low-energy projection images L, so that synchronized H/L image acquisition corresponds to high- and low-energy emission as the source 22 and detector 24 orbit the imaged subject 20.

One problem with the alternating low/high-energy level approach to DE volume imaging described above relates to the resulting image quality, since only half of the number of projection images typically needed are acquired at each respective energy level. If the two subsets are used separately, each used for generating a corresponding volume image, the resulting reconstructed volumes have poor resolution and degraded image quality, with the likelihood of various imaging artifacts, such as view-aliasing for example.

Applicant has observed that the two subsets of dual-energy images, because they expose the same object with the same imaging geometry, are highly correlated with respect to scene content and anatomy position. Embodiments of the present disclosure provide methods for overcoming the problem of reduced image quality by synthesizing, for each low- and high-energy subset of projection images, a number of intermediate images that can use information from the alternate subset as well as information from adjacent images within the corresponding subset.

In order to better understand the image synthesis process, it is useful to consider first the subset of high-energy images. The same logic applied for this subset can then be used equivalently with the low-energy image subset.

Figure 2B:
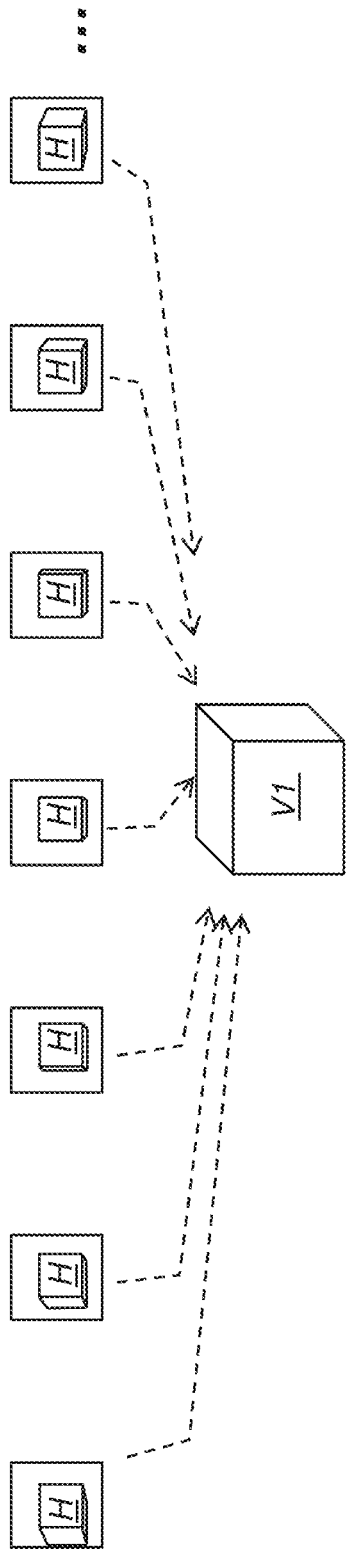
FIG. 2B is a schematic diagram that shows forming a coarse volume reconstruction for the high-energy portion of acquired images from FIG. 2A.

For the subset of $N_{high}$ high-energy 2D projections, for example, a coarse high-energy 3D reconstruction can initially be performed, forming an initial 3D volume image V1 as shown in FIG. 2B. One or more intermediate, synthesized projections, computed as described in more detail subsequently, can then be generated to supplement the subset of $N_{high}$ high-energy projections. Data from each actual, acquired projection from the subset of $N_{high}$ high-energy projections can be used to generate a subset of M intermediate projections; the combination of these two subsets of $N_{high}$ and M projections can form a set that thereby provides the full number of N+M 2D projections needed for a higher quality 3D volume reconstruction. A similar approach can be applied for the high-energy reconstruction sequence.

Figure 2C:
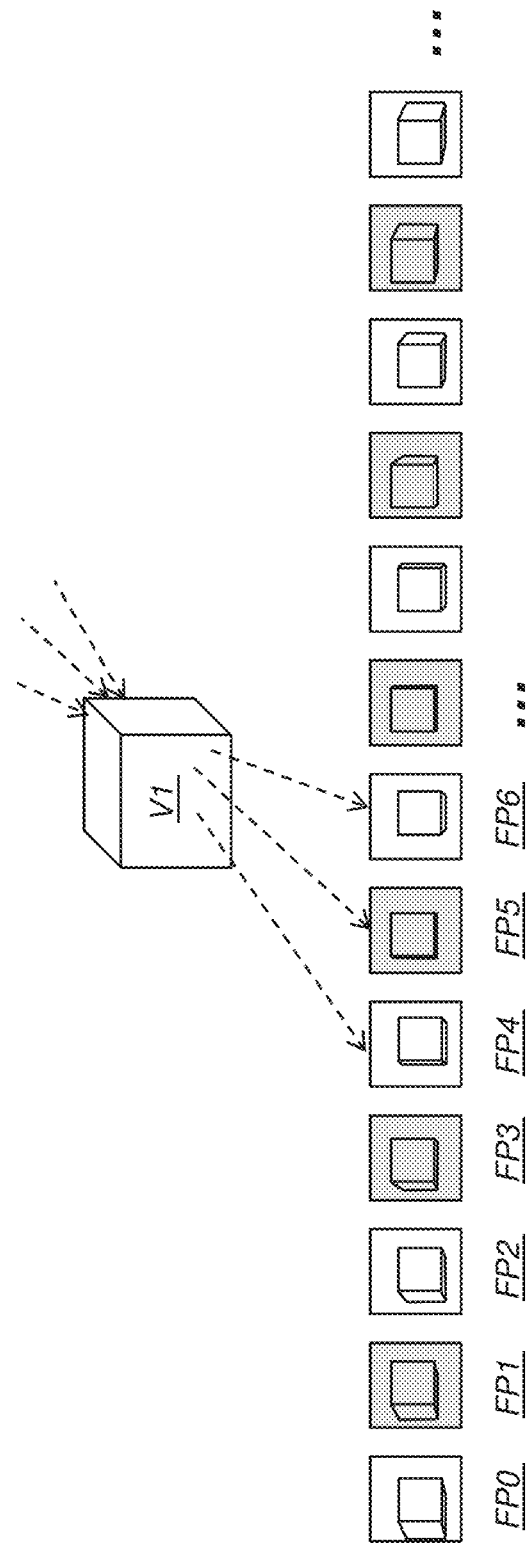
FIG. 2C is a schematic diagram showing the initial 3D reconstruction volume processed to generate intermediate synthetic images using forward projection.

As shown in the schematic of FIG. 2C, the initial 3D reconstruction, volume V1, is processed using forward projection. Volume V1 can be considered a coarse reconstruction, without the full set of images needed for more accurate reconstruction. Forward projection through the initial reconstructed volume V1 generates a set of forward projection images. The forward projection images are 2D projection images, designated FP0, FP1, FP2, FP3, FP4, FP5, FP6, . . . in FIG. 2C. As is shown by the relative spacing between the forward projection images FPn, these images are obtained at each of N+M projection angles. In the notation used in FIGS. 2C and 2B, the even-numbered forward projection images FP0, FP2, FP4, FP6, . . . are at angles corresponding to the image acquisition angles that were used for obtaining the subset of $N_{high}$ high-energy 2D projections H. Odd-numbered projections FP1, FP3, FP5, . . . are at angles not in the original subset of $N_{high}$ projection images; the odd-numbered projections correspond to the image acquisition angles used for the alternate subset of $N_{low}$ low-energy 2D projections L, as shown in FIG. 2A. The odd-numbered projections FP1, FP3, FP5, . . . are then processed in order to generate corresponding intermediate synthetic images S1, S3, S5, . . . . These intermediate synthetic images provide intermediate image content between the actual acquired images, complementing the $N_{high}$ subset of projection images to effectively provide N+M images, allowing a high resolution, high quality reconstruction to be obtained.

Generating and Using Synthetic Images

An embodiment of the present disclosure provides a method for improving reconstruction results without additional exposure to the patient by generating synthesized images that are formed using forward projection and an image data mapping sequence. As noted previously, the synthetic images that are thus formed can then be used to supplement the image content provided from actual acquired projection images for each subset of the dual-energy images, providing sufficient projection data to allow good quality dual-energy volume reconstruction without additional exposure to the patient.

Figure 3A:
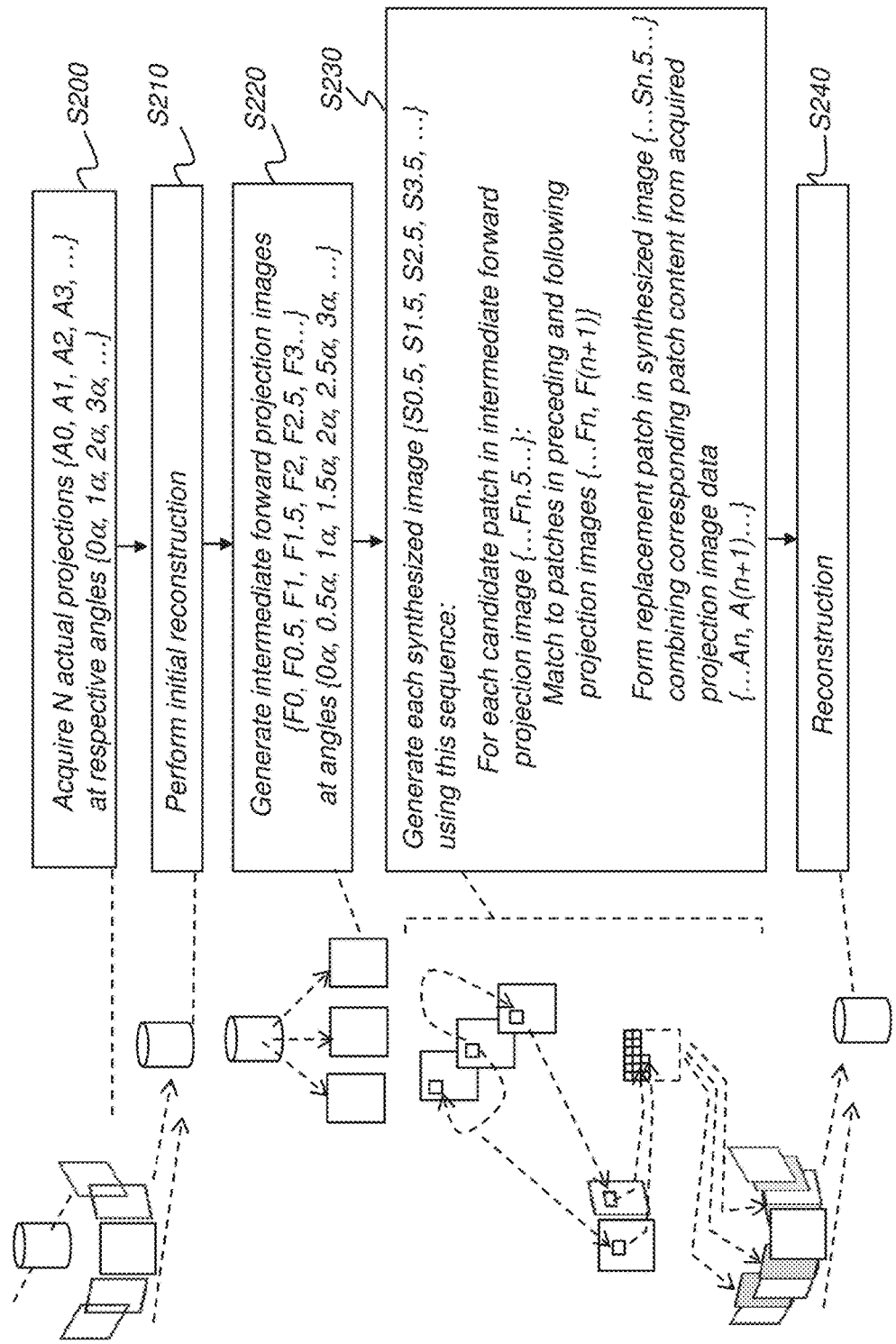
FIG. 3A is a logic flow diagram showing a basic sequence for enhanced dual-energy 3D reconstruction.

FIG. 3A is a logic flow diagram showing an overview of the basic sequence for forming and using synthetic images for enhanced volume reconstruction. In the context of the present disclosure, this sequence is described for use in forming synthetic images for the high-energy image content; it should be noted that equivalent processing, with the corresponding changes, would be used in similar manner for forming synthetic images for the low-energy content.

In an acquisition step S200, an ordered set having a number N of actual high-energy X-ray projection images {A0, A1, A2, A3, . . . }, termed the "acquired" images in the context of the present disclosure, is obtained. Each X-ray projection image in the set is acquired at one of a corresponding sequence of N capture angles α as indicated in FIG. 1. The ordered set of N acquired X-ray projection images can be considered ordered according to acquisition angle nα where n represents an integer. In practice, X-ray projection images can be acquired in any order with respect to angle; the ordered set structure is convenient arrangement for showing the acquisition sequence and for illustrating the processing that follows, used to generate synthesized images.

In the example process shown in FIG. 3A, every acquired X-ray projection image An has a corresponding capture angle $α_n$ (alternately expressed as nα) and is adjacent to a previous acquired X-ray projection image (n−1) with corresponding capture angle $α_{n-1}$ (alternately (n−1)α) and to a subsequent or following acquired X-ray projection image (n+1) with corresponding capture angle $α_{n+1}$ (alternately (n+1)α) Angular spacing between any two adjacent acquired X-ray projection images An in the sequence can be expressed as Δα and this spacing can be at equal intervals. From the ordered set of acquired projection images, an initial reconstruction step S210 forms a 3D volume image using an analytic reconstruction method such as filtered back projection (FBP), or using an iterative reconstruction process, or using some other suitable reconstruction algorithm.

In order to generate an expanded set of projection images for reconstruction, the procedural sequence of FIG. 3A performs a forward projection step S220 that generates an intermediate set of N+M forward projection images, shown in FIG. 3A and described herein as {F0, F0.5, F1, F1.5, F2, F2.5, F3 . . . } at corresponding angles {0 α, 0.5 α, 1 α, 1.5 α, 2 α, 2.5 α, 3α, . . . }. As used herein, the notation using "0.5" indicates angles between the acquisition angles α, such as half-way between. Forward projection thus generates projection images at each of the angles α corresponding to the N actual X-ray projections used for the high-energy images and adds M additional projection images at intermediate angles, such as at angles n.5 α, half-way between the original angles α. It should be emphasized that the intermediate angles can be at other than half-way between acquisition angle, such as at ⅓ intervals or at some arbitrary angular offset between the nearest acquired images. However, in order to take advantage of the high correlation of alternating low-energy images with the forward projection images, The half-way angle appears to work well.

Continuing with the FIG. 3A sequence, the process then proceeds to re-build a set of M synthesized projection images {S0.5, S1.5, S2.5, S3.5, . . . } using the M added projection images as initial templates in a synthesized image generation step S230.

Figure 3B:
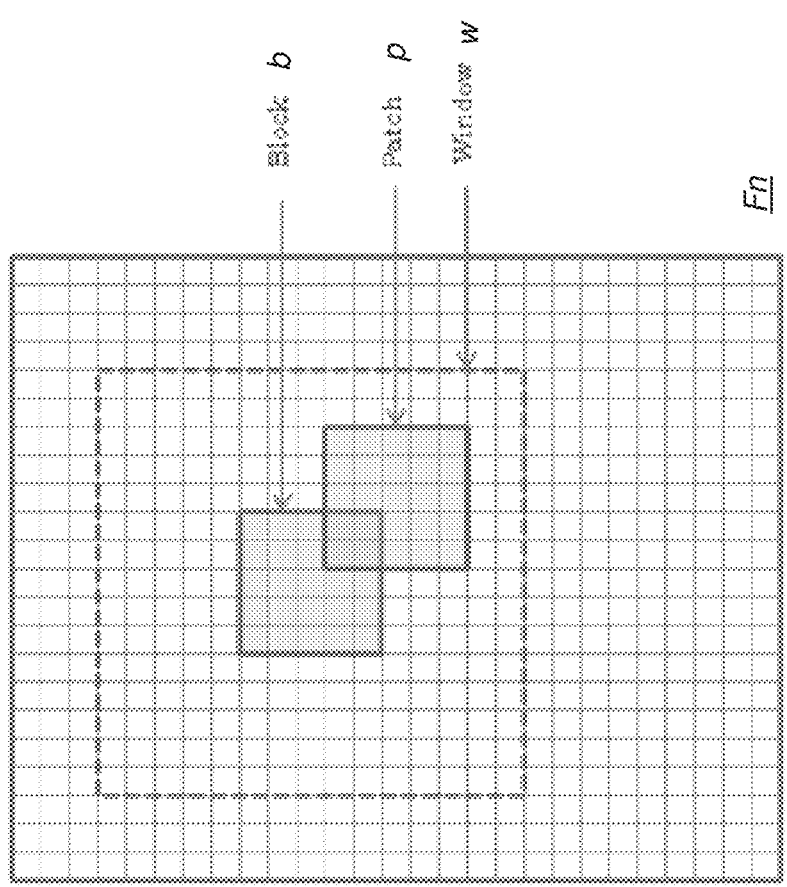
FIG. 3B is a schematic diagram showing the use of patches and window in block-matching according to an embodiment.

Synthesized image generation step S230 of FIG. 3A proceeds as follows:

a) Each of the M additional forward projection images is segmented into an array of patches p of a predetermined patch size, such as 5×5 pixels, 7×7 pixels, or other suitable size, as represented in FIG. 3B.

b) Each segmented patch p is mapped to its best matching patch in preceding and following forward projection images. Notationally, this can be considered as matching patch p in additional forward projection image Fn.5 to the corresponding image patch in preceding forward projection image Fn and in subsequent forward projection image F(n+1). Thus, for example, patch p in additional forward projection image F3.5 is matched with the corresponding patch in preceding forward projection image F3 and with the corresponding patch in subsequent forward projection image F4. Matching is performed by examining suitably sized blocks b within a larger window w. As shown by way of example in FIG. 3B, a window, such as a 27×22 or 21×21 pixel window, is used to define a search area for the patch in each forward projection image. Any of a number of commonly used image matching metrics, also termed "comparison metrics", can be employed to measure patch similarity.

c) Note that the preceding forward projection image Fn is at the same angle α as the original acquired x-ray projection image An; similarly, the subsequent forward projection image F(n+1) is at the same angle (n+1)a as the original acquired x-ray projection image A(n+1). Thus, for example, preceding forward projection image F3 is at the same angle 3α as the original acquired x-ray projection image A3; the subsequent forward projection image F4 is at the same angle 4α as the original acquired x-ray projection image A4.

d) Patch p in the additional forward projection image Fn.5 is then replaced with updated content using the mapped patch data from the original acquired x-ray projection images An and A(n+1). This patch data from the original acquired x-ray projection images An and A(n+1) is combined in some way, such as averaged or weighted-averaged, in order to form the new data that replaces patch p from the additional forward projection image Fn.5. Thus, for example, to reconstitute patch p in additional forward projection image F3.5, the matching patch content from original acquired x-ray projection images A3 and A4 can be combined, such as averaged for example.

The block-matching procedure given in steps a) through d) above is repeated for each patch p from the additional forward projection image Fn.5 until the additional forward projection image Fn.5 is fully formed as synthesized image Sn.5. This process is then repeated for the next additional forward projection image F(n+1).5 until all of the additional forward projection images are transformed into corresponding synthesized images {S0.5, S1.5, S2.5, S3.5, . . . }. The synthesized images Sn.5 can themselves be transmitted, stored, or displayed as needed.

Alternatively, synthesized projection images can be generated using other methods, such as a bidirectional interpolation method, for example. This method, familiar to those skilled in the image reconstruction arts, uses an averaging or weighting of adjacently acquired images to form the intermediate synthesized image for an intermediate angle between the two respective adjacent acquisition angles. The corresponding low-energy projections can be used to further condition or to generate corresponding high-energy intermediate synthetic projection images.

As was shown and described with reference to FIGS. 2A, 2B, and 2C, image acquisition obtains a subset of $N_{low}$ low-energy images along with members of the subset of $N_{high}$ high-energy images, with the two subsets interspersed with respect to angle. In terms of angle and scene content, each of the synthetic images that are formed to supplement the subset of $N_{high}$ high-energy images corresponds to one of the $N_{low}$ low-energy images. That is, the $N_{low}$ images are at the same angles used for the synthetic images that are formed to supplement the $N_{high}$ images. Similarly, the $N_{high}$ images are at the same angles used for the synthetic images that are formed to supplement the $N_{low}$ images. This correspondence can be used to help correct errors in synthetic image formation, helping to correlate the spatial content of the synthetic images with the acquired images of the alternate subset.

To continue the sequence of FIG. 3A, the synthesis process provides the needed image content for a final reconstruction step S240. In reconstruction, a 3D volume is generated using the original acquired X-ray projection images {A0, A1, A2, A3, . . . } supplemented by the set of interspersed synthesized images {S0.5, S1.5, S2.5, S3.5, . . . } that have been formed using the process described in FIG. 3A. The final reconstruction step S240 thus uses the combined set {A0, S0.5, A1, S1.5, A2, S2.5, A3, S3.5, . . . } for forming an enhanced 3D reconstruction.

According to the present disclosure, processing of steps S210, S220, and S230 repeats for the subset of $N_{low}$ low-energy images, generating projection image content that can be combined with results from processing the subset of $N_{high}$ high-energy images. The result can be a dual-energy volume reconstruction, as described in more detail subsequently.

Figure 4A:
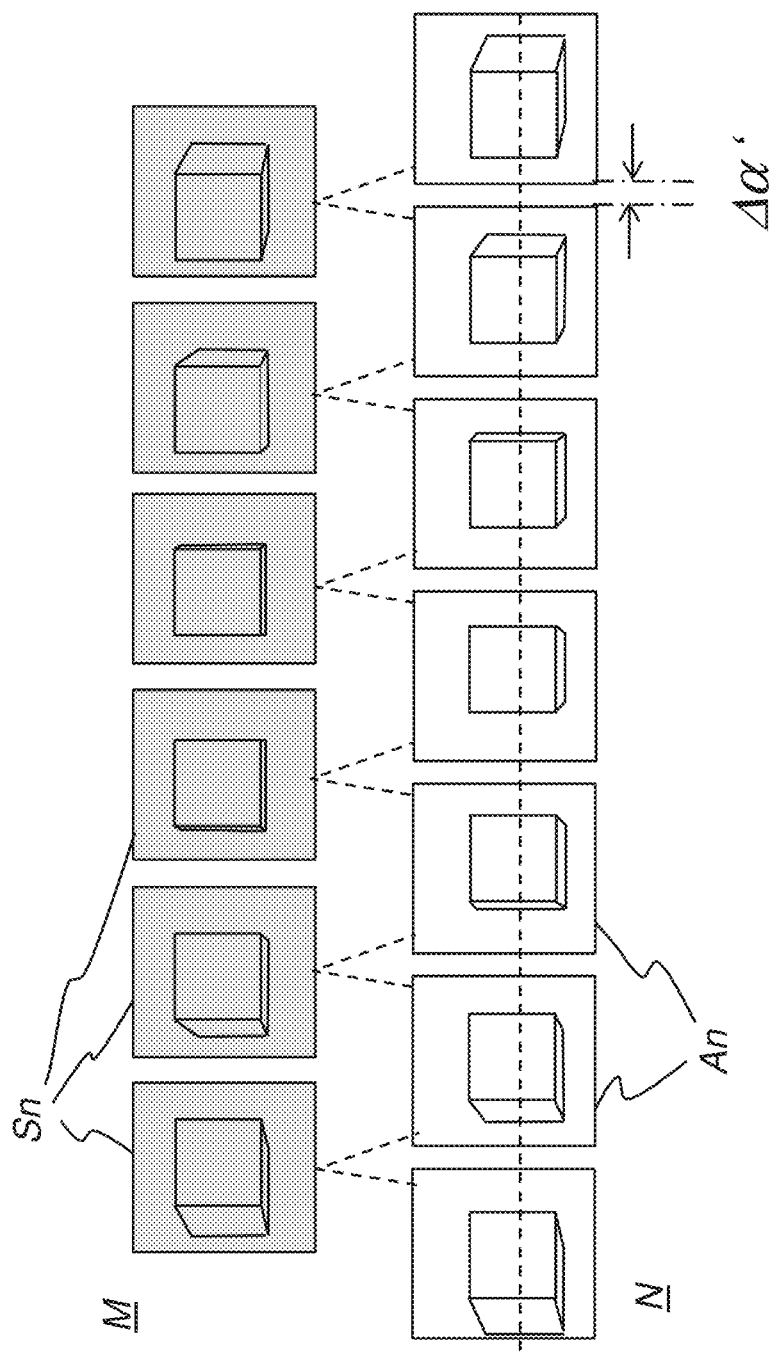
FIG. 4A is a schematic diagram that shows supplementing the ordered set of acquired X-ray projection images with a set of synthesized images.

FIG. 4A is a schematic diagram that shows supplementing the ordered set of N acquired X-ray projection images An with a set of M synthesized images Sn, in an interspersed manner.

Figure 4B:
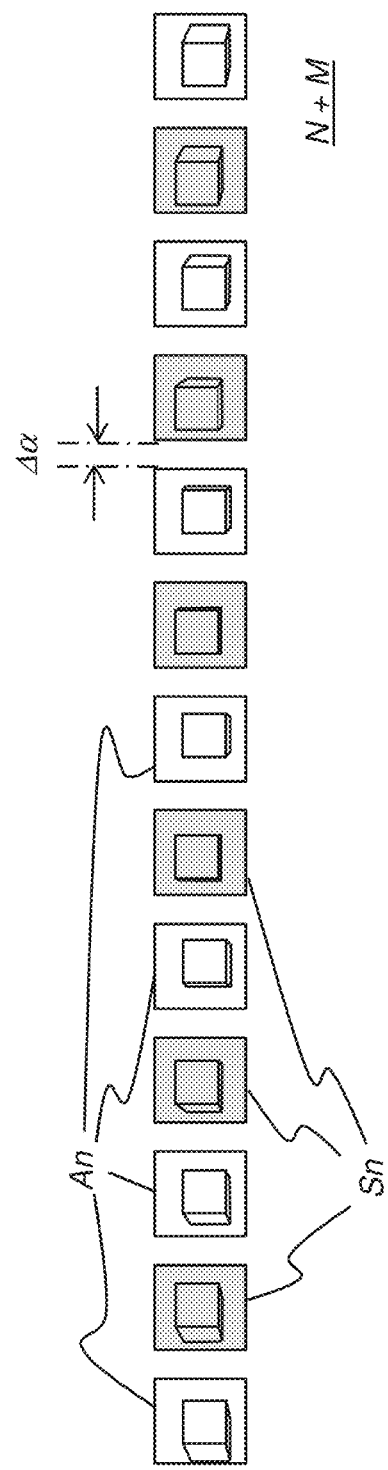
FIG. 4B is a schematic diagram that shows a combined set of acquired X-ray and intermediate synthesized images used for volume image reconstruction.

FIG. 4B is a schematic diagram that shows a combined set of acquired X-ray and intermediate synthesized images, An and Sn respectively, used for volume image reconstruction.

Within each subset, it should be noted that the number M of synthesized projection images that is generated can be smaller than, equal to, or even larger than the number N of actual X-ray projection images. Examples given following show generation of a single synthesized image M corresponding to an angle midway between the corresponding angles of first and second adjacent X-ray projection images n and (n+1); the image obtained at this midway angle is represented herein using the notation n.5. Thus, in the examples shown here, M<N. However, multiple synthesized images M can be generated for angles between any two adjacent X-ray projection images n and (n+1). For example, using the same processing approach, two synthesized images M can be generated between any two adjacent acquired X-ray projection images n and (n+1).

In order to further improve the quality of the synthetic projections, the expected correlation between the synthetic and actual projections can be applied in order to improve the synthetic projections. This can be implemented by setting a threshold, and if the correlation of a patch in the formation of the synthetic projection is below the threshold, then the alternative method for selecting a block is performed; alternately, if the correlation is superior, the generated forward projection data is used over the initial block selection.

Once the two sets of projections are completed a dual-energy reconstruction can be performed. This can result in a high-quality reconstruction with half the dose and half the time required for the patient to undergo the conventional dual-energy scanning process.

Dual-Energy Reconstruction

Figure 5:
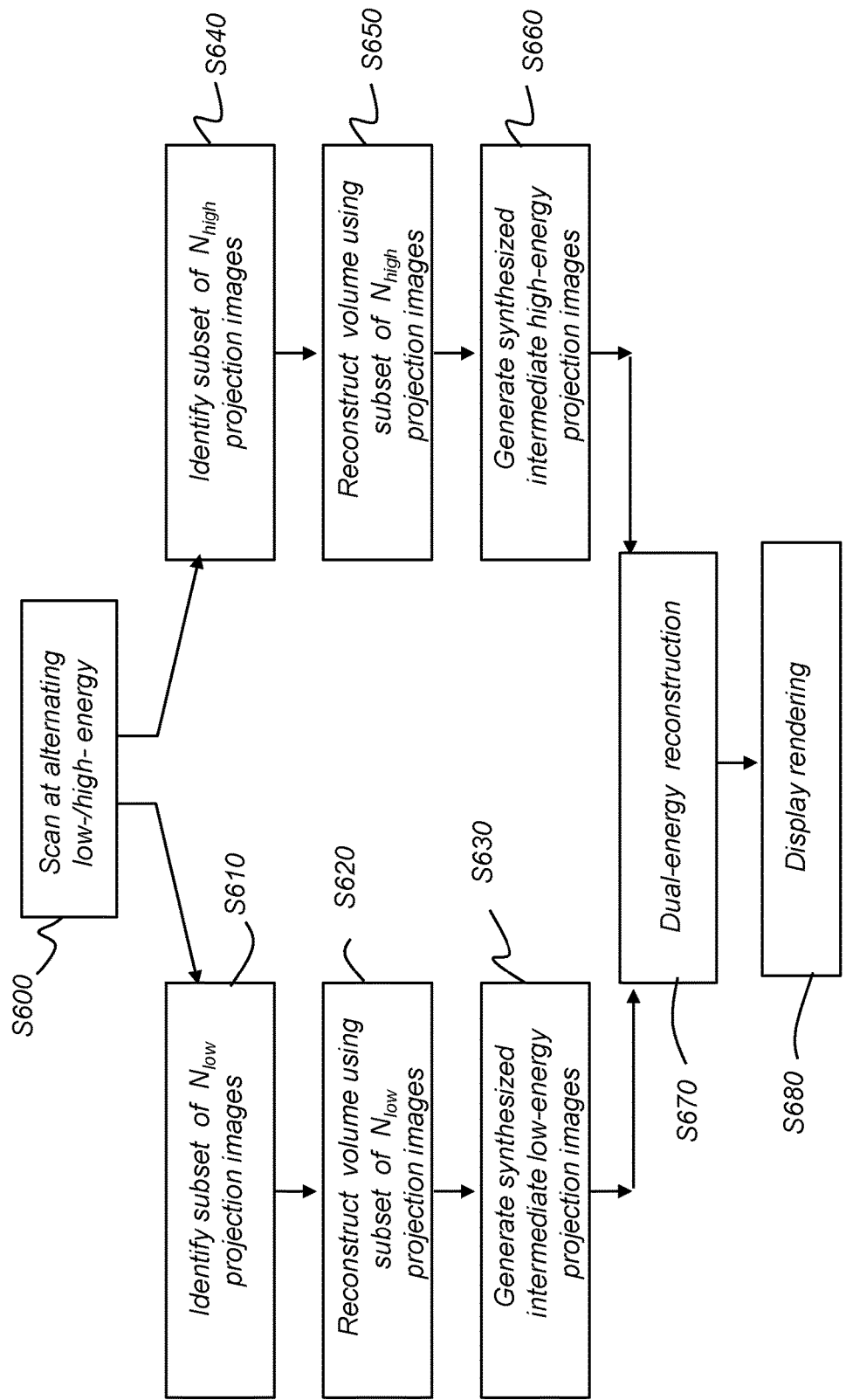
FIG. 5 is a logic flow diagram that shows a sequence of steps for forming a dual-energy reconstruction according to an embodiment of the present disclosure.

The logic flow diagram of FIG. 5 shows a sequence of steps for forming a dual-energy reconstruction according to an embodiment of the present disclosure. A scan step S600 executes, acquiring a sequence of 2D projection images, with alternating low- and high-energy images H/L obtained at angular intervals Δα as shown in FIG. 2A. Identification steps S640 and S610 separate the H and L images into two subsets, having $N_{high}$ and $N_{low}$ images, respectively, as described previously. For the low-energy projection images L, a coarse volume reconstruction step S620 uses the appropriate subset of $N_{low}$ projection images to form a low-energy volume image. Then, in synthesized image generation step S630, synthesized intermediate 2D projection images are obtained, calculated using forward projection as described previously with reference to step S230 in FIG. 3A.

Similarly, for the high-energy projection images H, a coarse volume reconstruction step S650 uses the appropriate subset of $N_{high}$ projection images to form a high-energy volume image. Then, in synthesized image generation step S660, synthesized intermediate 2D projection images are obtained, calculated using forward projection as described previously with reference to step S230 in FIG. 3A.

A dual-energy reconstruction can then be generated in a reconstruction step S670, forming a dual-energy volume using synthesized image results from corresponding steps S630 and S660 along with the originally generated subsets of $N_{low}$ and $N_{high}$ acquired images. A display rendering step S680 then allows the viewer to display 2D slices that have been rendered for display from the reconstructed dual-energy volume image of step S670.

Seam Smoothing

A synthesized image constructed using the method described herein can be formed as a mosaic of patches. Often, boundaries or seams between patches are readily discernable, causing perceptible degradation in the final reconstruction volume. One method to correct for seams is to perform a one dimensional smoothing filter across the seams. If the filter is applied uniformly, however, some sharp edges are overly smoothed and can clash with the actual images.

According to a method of the present disclosure, seam smoothing is executed with respect to the forward projected image. The synthesized image seams are smoothed by applying the following one directional algorithm vertically and horizontally:

(i) Identify adjacent pixels p1 and p2, each belonging to a different block.

(ii) Calculate the difference ΔSyn of the two pixels, p1 and p2.

(iii) Calculate the difference ΔAct, of pixels in the same location in the forward projected image.

(iii) Compare ΔSyn, and ΔAct. If |ΔSyn|<|ΔAct|, then make no change to pixel values; otherwise add one-third of the difference to pixel p1 and remove one third of the difference from p2.

The approach outlined above can help to dampen the seam boundary adaptively and can limit image degradation that can otherwise occur with a global smoothing approach.

Figure 6:
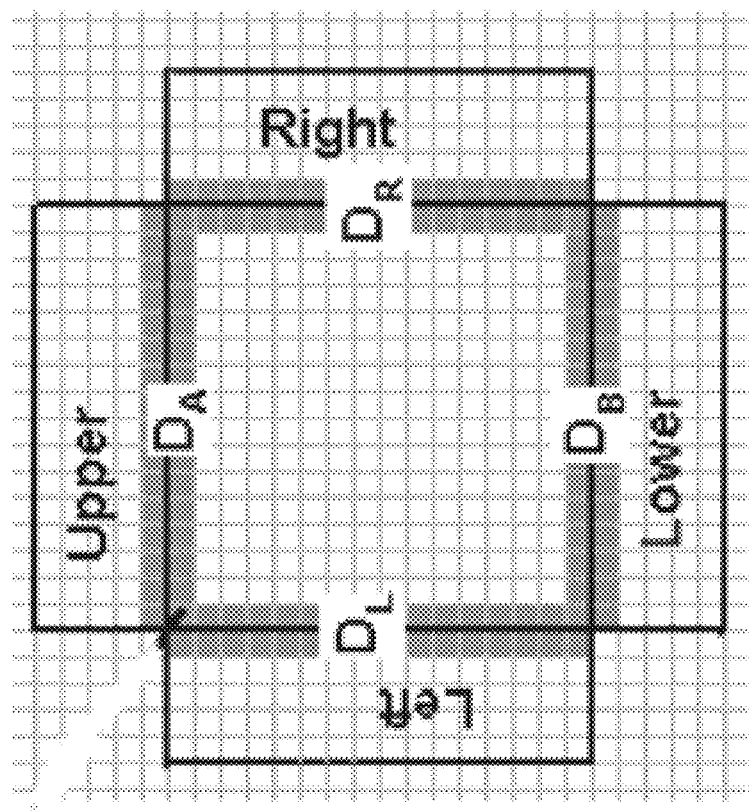
FIG. 6 shows the meaning of boundary matching terms $D_A$, $D_R$, $D_B$, $D_L$, used herein.

To help mitigate blocking artifacts, the Applicants can alternately use an improved spatial similarity metric, formed by adding terms that encourage spatial correlation with neighboring patches. This includes two types of terms: a boundary matching energy and a flow field smoothing energy. FIG. 6 shows the meaning of boundary matching terms $D_A$, $D_R$, $D_B$, $D_L$, used herein.

The basic energy relationship E can be expressed as follows:

$$E = \text{block matching energy} + \text{boundary matching energy} + \text{flow field smoothing energy} \quad (1)$$

Block matching energy can then be formulated as follows:

$$E_{blockmatching} = \sum_{(x,y) \in S(B)} |f_{left}(x-u, y-v) - f_{right}(x+u, y+v)| \quad (2)$$

A flow field term expresses the consistency of flow direction:

$$E_{flow\ field} = \sum_{i \in neighbors} |(u - u_i)| + |v - v_i| \quad (3)$$

where, as shown in FIG. 5:

$$neighbors = \{upper, lower, left, right\} \quad (4)$$

$$E_{boundary\ matching} = D_A + D_B + D_L + D_R \quad (5)$$

$$D_A(u, v) = \quad (6)$$
$$\sum_{x=0}^{N-1} |0.5(f_{left}(x - u, y - v) - f_{right}(x + u, y + v)) - f^{k-1}(x, y - 1)|$$

Embodiments of the present disclosure show improvement over earlier interpolation methods, particularly with respect to reduction of artifacts in general, particularly view aliasing artifacts.

Processing for analyzing acquired projection images can be performed, for example, by computer 30, as shown in FIG. 1.

Consistent with one embodiment, the present disclosure utilizes a computer program with stored instructions that perform on image data accessed from an electronic memory. As can be appreciated by those skilled in the image processing arts, a computer program of an embodiment of the present invention can be utilized by a suitable, general-purpose computer system, such as a personal computer or workstation. However, many other types of computer systems can be used to execute the computer program of the present invention, including networked processors. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Displaying an image requires memory storage. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. An imaging method, comprising:
    accessing a set of low-energy projection images of a subject, the set of low-energy projection images ordered in a sequence according to a low-energy projection capture angle therefor;
    reconstructing a low-energy image of the subject using the ordered set of low-energy projection images of the subject;
    synthesizing an intermediate low-energy projection image of the subject for each adjacent pair of the ordered set of low-energy projection images using the reconstructed low-energy image of the subject, including synthesizing the intermediate low-energy projection image of the subject at a low-energy synthesized capture angle intermediate to the low-energy projection capture angles of a corresponding adjacent pair of the ordered set of low-energy projection images;
    accessing a set of high-energy projection images of the subject, the set of high-energy projection images ordered in a sequence according to a high-energy projection capture angle therefor, each of the high-energy projection capture angles different from all of the low-energy projection capture angles;
    reconstructing a high-energy image of the subject using the ordered set of high-energy projection images of the subject;
    synthesizing an intermediate high-energy projection image of the subject for each adjacent pair of the ordered set of high-energy projection images using the reconstructed high-energy image of the subject, including synthesizing the intermediate high-energy projection image of the subject at a high-energy synthesized capture angle intermediate to the high-energy projection capture angles of a corresponding adjacent pair of the ordered set of high-energy projection images; and reconstructing a dual-energy image of the subject using the set of low-energy projection images of the subject, the synthesized intermediate low-energy projection image of the subject for each adjacent pair of the ordered set of low-energy projection images of the subject, the set of high-energy projection images of the subject, and the synthesized intermediate high-energy projection image of the subject for each adjacent pair of the ordered set of high-energy projection images of the subject.

2. The method of claim 1, wherein the step of synthesizing an intermediate low-energy projection image of the subject includes applying a synthesized forward projection method to the reconstructed low-energy image of the subject.

3. The method of claim 2, wherein applying the synthesized forward projection method includes applying either a bidirectional method or a block matching method.

4. The method of claim 1, wherein the step of synthesizing an intermediate high-energy projection image of the subject includes applying a synthesized projection method to the reconstructed high-energy image of the subject.

5. The method of claim 4, wherein applying the synthesized projection method includes applying either a bidirectional method or a block matching method.

6. A computer storage product having at least one computer storage medium having instructions stored therein causing one or more computers to perform the method of claim 1.

7. The method of claim 1, wherein the step of synthesizing an intermediate low-energy projection image of the subject for each adjacent pair of the ordered set of low-energy projection images includes synthesizing the intermediate low-energy projection image of the subject at a low-energy synthesized capture angle half-way between the low-energy projection capture angles of the corresponding adjacent pair of the ordered set of low-energy projection images.

8. The method of claim 1, wherein the step of synthesizing an intermediate high-energy projection image of the subject for each adjacent pair of the ordered set of high-energy projection images includes synthesizing the intermediate high-energy projection image of the subject at a high-energy synthesized capture angle half-way between the high-energy projection capture angles of the corresponding adjacent pair of the ordered set of high-energy projection images.

9. An imaging method, comprising:

accessing a first set of projection images of a subject, the first set of projection images comprising low-energy projection images of the subject, wherein each low-energy projection image of the subject was captured at a different corresponding low-energy acquisition angle;

reconstructing a low-energy volume image of the subject using the low-energy projection images of the subject;

synthesizing a second set of projection images of the subject, the second set of projection images comprising intermediate low-energy synthesized projection images of the subject each synthesized at an angle intermediate to two of the low-energy acquisition angles of the low-energy projection images of the subject;

accessing a third set of projection images of the subject, the third set of projection images comprising high-energy projection images of the subject, wherein each high-energy projection image of the subject was captured at a different corresponding high-energy acquisition angle, and wherein each corresponding high-energy acquisition angle is different from all of the acquisition angles corresponding to the first set of projection images of the subject;

reconstructing a high-energy volume image of the subject using the high-energy projection images of the subject;

synthesizing a fourth set of projection images of the subject, the fourth set of projection images comprising intermediate high-energy synthesized projection images of the subject each synthesized at an angle intermediate to two of the high-energy acquisition angles of the high-energy projection images of the subject; and reconstructing a volume dual-energy image of the subject using each of the first, second, third, and fourth sets of projection images of the subject.

10. The method of claim 9, further comprising acquiring the first set and the third set of projection images of the subject using an x-ray source alternating between emitting a first x-ray energy level and a second x-ray energy level during an x-ray scan of the subject.

11. The method of claim 9, wherein the step of synthesizing a second set of projection images of the subject includes forward projecting the reconstructed low-energy volume image of the subject.

12. The method of claim 11, wherein the step of forward projecting the reconstructed low-energy volume image of the subject includes applying either a bidirectional method or a block matching method.

13. The method of claim 9, wherein the step of synthesizing a fourth set of projection images of the subject includes forward projecting the reconstructed high-energy volume image of the subject.

14. The method of claim 13, wherein the step of forward projecting the reconstructed high-energy volume image of the subject includes applying either a bidirectional method or a block matching method.

15. A computer storage product having at least one non-transitory computer storage medium having instructions stored therein causing one or more computers to perform the method of claim 9.

16. The method of claim 9, wherein the step of synthesizing a second set of projection images of the subject includes synthesizing at an angle half-way between two of the low-energy acquisition angles of the low-energy projection images of the subject.

17. The method of claim 9, wherein the step of synthesizing a fourth set of projection images of the subject includes synthesizing at an angle half-way between two of the high-energy acquisition angles of the high-energy projection images of the subject.

* * * * *